(12) United States Patent
Alshaiba Saleh Ghannam Almazrouei et al.

(10) Patent No.: US 12,213,516 B2
(45) Date of Patent: Feb. 4, 2025

(54) ULTRASONIC MIST INHALER (71) Applicant: SHAHEEN INNOVATIONS HOLDING LIMITED, Abu Dhabi (AE)

(72) Inventors: Mohammed Alshaiba Saleh Ghannam Almazrouei, Abu Dhabi (AE); Imad Lahoud, Abu Dhabi (AE)

(73) Assignee: Shaheen Innovations Holding Limited, Abu Dhabi (AE)

( * ) Notice: Subject to any disclaimer, the term of this patent is extended or adjusted under 35 U.S.C. 154(b) by 226 days.

(21) Appl. No.: 17/772,358

(22) PCT Filed: Dec. 15, 2019

(86) PCT No.: PCT/IB2019/060807
§ 371 (c)(1),
(2) Date: Apr. 27, 2022

(87) PCT Pub. No.: WO2021/123866
PCT Pub. Date: Jun. 24, 2021

(65) Prior Publication Data
US 2022/0400746 A1 Dec. 22, 2022

(51) Int. Cl.
*A24F 40/05* (2020.01)
*A24B 15/167* (2020.01)
(Continued)

(52) U.S. Cl.
CPC ............ *A24F 40/05* (2020.01); *A24B 15/167* (2016.11); *A24F 7/00* (2013.01); *A24F 40/10* (2020.01); *A24F 40/42* (2020.01); *A24F 40/44* (2020.01); *A24F 40/48* (2020.01); *A61M 15/0021* (2014.02); *A61M 15/0066* (2014.02); *A61M 15/0085* (2013.01); *A61M 15/0086* (2013.01);
(Continued)

(58) Field of Classification Search
None
See application file for complete search history.

(56) References Cited

U.S. PATENT DOCUMENTS 4,119,096 A 10/1978 Drews
4,334,531 A 6/1982 Reichl
(Continued)

FOREIGN PATENT DOCUMENTS

CN 101648041 A 2/2010
CN 104055225 A 9/2014
(Continued)

OTHER PUBLICATIONS

English machine translation of WO-2004080216-A1; Hon; Sep. 23, 2004, 12 pages. (Year: 2004).*
(Continued)

*Primary Examiner* — Linda L Gray
(74) *Attorney, Agent, or Firm* — Amedeo F. Ferraro, Esq.

(57) ABSTRACT

The invention relates to an ultrasonic mist inhaler (100), comprising: a mouthpiece (1) for inhaling the mist, a liquid reservoir structure (2) comprising a liquid chamber (21) adapted to receive liquid to be atomized, a sonication chamber (22) in fluid communication with the liquid chamber (21), wherein at least part of the liquid reservoir structure (2) and the mouthpiece (1) form the sonication chamber (22).

11 Claims, 4 Drawing Sheets

(51) Int. Cl.
  *A24F 7/00* (2006.01)
  *A24F 40/10* (2020.01)
  *A24F 40/42* (2020.01)
  *A24F 40/44* (2020.01)
  *A24F 40/48* (2020.01)
  *A61M 15/00* (2006.01)
  *A61M 15/06* (2006.01)
  *B05B 12/00* (2018.01)
  *B05B 17/00* (2006.01)
  *B05B 17/06* (2006.01)

(52) U.S. Cl.
  CPC ......... *A61M 15/06* (2013.01); *B05B 17/0684* (2013.01); *B05B 12/008* (2013.01)

(56) References Cited

U.S. PATENT DOCUMENTS

| | | |
|---|---|---|
| 5,355,873 A | 10/1994 | Del Bon |
| 5,518,179 A | 5/1996 | Humberstone et al. |
| 5,551,416 A | 9/1996 | Stimpson |
| 5,894,841 A | 4/1999 | Voges |
| 5,950,619 A | 9/1999 | van der Linden |
| 6,011,345 A | 1/2000 | Murray |
| 6,040,560 A | 3/2000 | Fleischhauer |
| 6,402,046 B1 | 6/2002 | Loeser |
| 6,601,581 B1 | 8/2003 | Babaev |
| 6,679,436 B1 | 1/2004 | Onishi |
| 7,129,619 B2 | 10/2006 | Yang |
| 8,991,722 B2 | 3/2015 | Friend |
| 9,242,263 B1 | 1/2016 | Copeman |
| 9,278,365 B2 | 3/2016 | Banco |
| 9,415,412 B2 | 8/2016 | Kawashima |
| 9,687,029 B2 | 6/2017 | Liu |
| 9,687,627 B2 | 6/2017 | Gallem |
| 9,718,078 B1 | 8/2017 | Chau |
| 9,867,398 B2 | 1/2018 | Guo |
| 9,980,140 B1 | 5/2018 | Spencer |
| 10,034,495 B2 | 7/2018 | Alarcon |
| 10,071,391 B2 | 9/2018 | Yu |
| 10,195,368 B2 | 2/2019 | Wang |
| 10,300,225 B2 | 5/2019 | Terry |
| 10,327,479 B2 | 6/2019 | Popplewell |
| 10,328,218 B2 | 6/2019 | Reed |
| 10,412,996 B2 | 9/2019 | Bright |
| 10,506,827 B2 | 12/2019 | Liu |
| 10,561,803 B2 | 2/2020 | Liu |
| 10,617,150 B2 | 4/2020 | Cameron |
| 10,757,971 B2 | 9/2020 | Liu |
| 11,039,641 B2 | 6/2021 | Liu |
| 11,207,711 B2 | 12/2021 | Hejazi |
| 11,219,245 B2 | 1/2022 | Liu |
| 11,278,055 B2 | 3/2022 | Liu |
| 11,304,451 B2 | 4/2022 | Hejazi |
| 11,324,253 B2 | 5/2022 | Liu |
| 11,431,242 B2 | 8/2022 | Liu |
| 11,517,685 B2 | 12/2022 | Danek |
| 11,589,609 B2 | 2/2023 | Liu |
| 11,641,876 B2 | 5/2023 | Liu |
| 11,690,963 B2 | 7/2023 | Danek |
| 11,700,881 B2 | 7/2023 | Liu |
| 11,730,896 B2 | 8/2023 | Hutchins |
| 11,744,282 B2 | 9/2023 | Liu |
| 11,744,284 B2 | 9/2023 | Liu |
| 11,771,133 B2 | 10/2023 | Lin |
| 11,771,137 B2 | 10/2023 | Liu |
| 11,796,732 B2 | 10/2023 | Novak, III |
| 11,877,600 B2 | 1/2024 | Liu |
| 11,964,301 B2 | 4/2024 | Hejazi |
| 2002/0129813 A1 | 9/2002 | Litherland |
| 2003/0164545 A1 | 9/2003 | Nadd |
| 2003/0192532 A1 | 10/2003 | Hopkins |
| 2003/0209005 A1 | 11/2003 | Fenn |
| 2006/0243277 A1 | 11/2006 | Denyer |
| 2006/0243820 A1 | 11/2006 | Ng |
| 2007/0125370 A1 | 6/2007 | Denyer |
| 2008/0054091 A1 | 3/2008 | Babaev |
| 2008/0088202 A1 | 4/2008 | Duru |
| 2008/0156320 A1 | 7/2008 | Low |
| 2008/0164339 A1 | 7/2008 | Duru |
| 2009/0022669 A1 | 1/2009 | Waters |
| 2009/0065600 A1 | 3/2009 | Tranchant |
| 2010/0084488 A1 | 4/2010 | Mahoney, III |
| 2010/0139652 A1 | 6/2010 | Lipp |
| 2011/0012677 A1 | 1/2011 | Lutsen Ludgerus |
| 2012/0126041 A1 | 5/2012 | Mahito et al. |
| 2013/0220315 A1 | 8/2013 | Conley |
| 2014/0007864 A1 | 1/2014 | Gordon |
| 2014/0151457 A1 | 6/2014 | Wilkerson |
| 2014/0261414 A1 | 9/2014 | Weitzel |
| 2014/0270727 A1 | 9/2014 | Ampolini |
| 2015/0069146 A1 | 3/2015 | Lowy |
| 2015/0202387 A1 | 7/2015 | Yu |
| 2015/0230522 A1 | 8/2015 | Horn |
| 2015/0231347 A1 | 8/2015 | Gumaste |
| 2015/0272214 A1 | 10/2015 | Giller |
| 2016/0001316 A1 | 1/2016 | Friend |
| 2016/0066619 A1 | 3/2016 | Di Carlo |
| 2016/0089508 A1 | 3/2016 | Smith |
| 2016/0198770 A1 | 7/2016 | Alarcon |
| 2016/0199594 A1 | 7/2016 | Finger |
| 2016/0206001 A1 | 7/2016 | Eng |
| 2016/0213866 A1 | 7/2016 | Tan |
| 2016/0264290 A1 | 9/2016 | Hafer |
| 2016/0324212 A1 | 11/2016 | Cameron |
| 2016/0331022 A1 | 11/2016 | Cameron |
| 2016/0338407 A1 | 11/2016 | Kerdemelidis |
| 2017/0042242 A1 | 2/2017 | Hon |
| 2017/0119052 A1 | 5/2017 | Williams |
| 2017/0119059 A1 | 5/2017 | Zuber |
| 2017/0135411 A1 | 5/2017 | Cameron |
| 2017/0136194 A1 | 5/2017 | Cameron |
| 2017/0136484 A1 | 5/2017 | Wilkerson |
| 2017/0251718 A1 | 9/2017 | Armoush |
| 2017/0265521 A1 | 9/2017 | Do |
| 2017/0281883 A1 | 10/2017 | Li |
| 2017/0303594 A1 | 10/2017 | Cameron |
| 2017/0368273 A1 | 12/2017 | Rubin |
| 2018/0042306 A1 | 2/2018 | Atkins |
| 2018/0153217 A1 | 6/2018 | Liu |
| 2018/0160737 A1 | 6/2018 | Verleur |
| 2018/0166981 A1 | 6/2018 | Leppard |
| 2018/0192702 A1 | 7/2018 | Li |
| 2018/0269867 A1 | 9/2018 | Terashima |
| 2018/0029677 A1 | 10/2018 | Terry |
| 2018/0286207 A1 | 10/2018 | Baker |
| 2018/0296777 A1 | 10/2018 | Terry |
| 2018/0296778 A1 | 10/2018 | Hacker |
| 2018/0310625 A1 | 11/2018 | Alarcon |
| 2018/0338532 A1 | 11/2018 | Verleur |
| 2018/0343926 A1 | 12/2018 | Wensley |
| 2019/0056131 A1 | 2/2019 | Warren |
| 2019/0098935 A1 | 4/2019 | Phan |
| 2019/0116863 A1 | 4/2019 | Dull |
| 2019/0133186 A1 | 5/2019 | Fraser |
| 2019/0158938 A1 | 5/2019 | Bowen |
| 2019/0166913 A1 | 6/2019 | Trzecieski |
| 2019/0167923 A1 | 6/2019 | Kessler |
| 2019/0216135 A1 | 7/2019 | Guo |
| 2019/0255554 A1 | 8/2019 | Selby |
| 2019/0289914 A1 | 9/2019 | Liu |
| 2019/0289915 A1 | 9/2019 | Heidl |
| 2019/0289918 A1 | 9/2019 | Hon |
| 2019/0321570 A1 | 10/2019 | Rubin |
| 2019/0329281 A1 | 10/2019 | Lin |
| 2019/0335580 A1 | 10/2019 | Lin |
| 2019/0336710 A1 | 11/2019 | Yamada |
| 2019/0037473 A1 | 12/2019 | Chen |
| 2019/0373679 A1 | 12/2019 | Fu |
| 2019/0374730 A1 | 12/2019 | Chen |
| 2019/0387795 A1 | 12/2019 | Fisher |
| 2020/0000143 A1 | 1/2020 | Anderson |
| 2020/0000146 A1 | 1/2020 | Anderson |
| 2020/0009600 A1 | 1/2020 | Tan |

(56) References Cited

U.S. PATENT DOCUMENTS

| | | | |
|---|---|---|---|
| 2020/0016344 | A1 | 1/2020 | Scheck |
| 2020/0022416 | A1 | 1/2020 | Alarcon |
| 2020/0046030 | A1 | 2/2020 | Krietzman |
| 2020/0068949 | A1 | 3/2020 | Rasmussen |
| 2020/0085100 | A1 | 3/2020 | Hoffman |
| 2020/0120989 | A1 | 4/2020 | Danek |
| 2020/0120991 | A1 | 4/2020 | Hatton |
| 2020/0146361 | A1 | 5/2020 | Silver |
| 2020/0178598 | A1 | 6/2020 | Mitchell |
| 2020/0178606 | A1 | 6/2020 | Liu |
| 2020/0214349 | A1 | 7/2020 | Liu |
| 2020/0221771 | A1 | 7/2020 | Atkins |
| 2020/0221776 | A1 | 7/2020 | Liu |
| 2020/0245692 | A1 | 8/2020 | Cameron |
| 2020/0345058 | A1 | 11/2020 | Bowen |
| 2020/0404975 | A1 | 12/2020 | Chen |
| 2021/0015957 | A1 | 1/2021 | Bush |
| 2021/0076733 | A1 | 3/2021 | Liu |
| 2021/0112858 | A1 | 4/2021 | Liu |
| 2021/0120880 | A1 | 4/2021 | Liu |
| 2021/0153548 | A1 | 5/2021 | Twite |
| 2021/0153549 | A1 | 5/2021 | Twite |
| 2021/0153564 | A1 | 5/2021 | Hourmand |
| 2021/0153565 | A1 | 5/2021 | Twite |
| 2021/0153566 | A1 | 5/2021 | Hourmand |
| 2021/0153567 | A1 | 5/2021 | Twite |
| 2021/0153568 | A1 | 5/2021 | Twite |
| 2021/0153569 | A1 | 5/2021 | Twite |
| 2021/0177056 | A1 | 6/2021 | Yilmaz |
| 2021/0212362 | A1 | 7/2021 | Liu |
| 2021/0378303 | A1 | 12/2021 | Liu |
| 2021/0401061 | A1 | 12/2021 | Davis |
| 2022/0030942 | A1 | 2/2022 | Lord |
| 2022/0151301 | A1 | 5/2022 | Liu |
| 2022/0240589 | A1 | 8/2022 | Liu |
| 2022/0273037 | A1 | 9/2022 | Liu |
| 2022/0279857 | A1 | 9/2022 | Liu |
| 2022/0287361 | A1 | 9/2022 | Kim |
| 2022/0295876 | A1 | 9/2022 | Liu |
| 2022/0395023 | A1 | 12/2022 | Liu |
| 2022/0400747 | A1 | 12/2022 | Liu |
| 2023/0001107 | A1 | 1/2023 | Connolly |
| 2023/0013741 | A1 | 1/2023 | Liu |
| 2023/0020762 | A1 | 1/2023 | Liu |
| 2023/0165303 | A1 | 6/2023 | Liu |
| 2023/0292839 | A1 | 9/2023 | Kim |

FOREIGN PATENT DOCUMENTS

| | | |
|---|---|---|
| CN | 204070580 U | 1/2015 |
| CN | 104640708 | 5/2015 |
| CN | 204499481 U | 7/2015 |
| CN | 105747277 A | 7/2016 |
| CN | 105768238 A | 7/2016 |
| CN | 105795526 A | 7/2016 |
| CN | 105876873 A | 8/2016 |
| CN | 205432145 U | 8/2016 |
| CN | 106108118 A | 11/2016 |
| CN | 205831074 A | 12/2016 |
| CN | 106422005 | 2/2017 |
| CN | 205947130 U | 2/2017 |
| CN | 206025223 U | 3/2017 |
| CN | 206043451 U | 3/2017 |
| CN | 206079025 U | 4/2017 |
| CN | 206119183 U | 4/2017 |
| CN | 206119184 U | 4/2017 |
| CN | 106617319 A | 5/2017 |
| CN | 206303211 U | 7/2017 |
| CN | 206333372 U | 7/2017 |
| CN | 107048479 A | 8/2017 |
| CN | 206586397 U | 10/2017 |
| CN | 206949536 U | 2/2018 |
| CN | 107822195 | 3/2018 |
| CN | 207185926 | 4/2018 |
| CN | 105476071 | 5/2018 |
| CN | 207383536 | 5/2018 |
| CN | 207400330 | 5/2018 |
| CN | 108283331 A | 7/2018 |
| CN | 108355210 A | 8/2018 |
| CN | 105876873 B | 12/2018 |
| CN | 109619655 A | 1/2019 |
| CN | 208354603 | 1/2019 |
| CN | 208434721 U | 1/2019 |
| CN | 106108118 B | 4/2019 |
| CN | 208837110 U | 5/2019 |
| CN | 209060228 U | 7/2019 |
| CN | 110150760 A | 8/2019 |
| CN | 209255084 U | 8/2019 |
| CN | 105876870 B | 11/2019 |
| CN | 209900345 U | 1/2020 |
| CN | 210076566 U | 2/2020 |
| CN | 210225387 | 3/2020 |
| CN | 110946315 A | 4/2020 |
| CN | 111229528 | 6/2020 |
| CN | 111838775 | 10/2020 |
| CN | 211675730 U | 10/2020 |
| CN | 212441811 | 2/2021 |
| CN | 214289213 | 9/2021 |
| CN | 214483267 | 10/2021 |
| CN | 215819888 | 2/2022 |
| CN | 217342045 | 9/2022 |
| CN | 217609513 | 10/2022 |
| CN | 217643921 U | 10/2022 |
| CN | 115336802 | 11/2022 |
| CN | 217826736 | 11/2022 |
| CN | 116807059 | 9/2023 |
| CN | 116850853 | 10/2023 |
| DE | 2656370 A1 | 6/1978 |
| DE | 2656370 B2 | 11/1978 |
| DE | 2656370 C3 | 7/1979 |
| DE | 100 51 792 A1 | 5/2002 |
| DE | 10122065 A1 | 12/2002 |
| EP | 0 258 637 A1 | 3/1988 |
| EP | 0 295 122 A2 | 12/1988 |
| EP | 0 258 637 B1 | 6/1990 |
| EP | 0 442 510 A1 | 8/1991 |
| EP | 0 442 510 B1 | 1/1995 |
| EP | 0 516 565 B1 | 4/1996 |
| EP | 0 824 927 A | 2/1998 |
| EP | 0 833 695 A1 | 4/1998 |
| EP | 0 845 220 A1 | 6/1998 |
| EP | 0 893 071 A1 | 1/1999 |
| EP | 0 970 627 A1 | 1/2000 |
| EP | 1083952 B1 | 12/2005 |
| EP | 1 618 803 B1 | 12/2008 |
| EP | 3 088 007 A1 | 11/2016 |
| EP | 3 192 381 A1 | 7/2017 |
| EP | 3 278 678 A1 | 2/2018 |
| EP | 3298912 A1 | 3/2018 |
| EP | 3 088 007 B1 | 11/2018 |
| EP | 3 434 118 A1 | 1/2019 |
| EP | 3 469 927 A1 | 4/2019 |
| EP | 3 505 098 | 7/2019 |
| EP | 3 520 634 A1 | 8/2019 |
| EP | 3 278 678 B1 | 10/2019 |
| EP | 3545778 A1 | 10/2019 |
| EP | 3 574 902 A1 | 12/2019 |
| EP | 3 516 971 | 3/2021 |
| EP | 3 528 651 | 5/2021 |
| EP | 3 837 999 A1 | 6/2021 |
| EP | 3 574 778 | 7/2021 |
| EP | 3 593 656 | 10/2021 |
| EP | 4252561 | 10/2023 |
| EP | 4033927 | 11/2023 |
| FR | 3043576 A1 | 5/2017 |
| FR | 3064502 A1 | 5/2018 |
| GB | 1 528 391 A | 10/1978 |
| GB | 2566766 A | 3/2019 |
| GB | 2570439 A | 7/2019 |
| JP | 05093575 U | 12/1993 |
| JP | 2579614 Y2 | 8/1998 |
| JP | 2001069963 A | 3/2001 |
| JP | 2005288400 A | 10/2005 |
| JP | 2008-104966 A | 5/2008 |

(56) References Cited

FOREIGN PATENT DOCUMENTS

| | | |
|---|---|---|
| JP | 2011-500160 | 1/2011 |
| JP | 2012-507208 | 3/2012 |
| JP | 2014-004042 | 1/2014 |
| JP | 2019515684 | 6/2019 |
| JP | 2019521671 A | 8/2019 |
| JP | 2019-524113 | 9/2019 |
| JP | 2019-526240 | 9/2019 |
| JP | 2019-526241 | 9/2019 |
| JP | 2020535846 A | 12/2020 |
| JP | 2022032444 | 2/2022 |
| KR | 20120107219 A | 10/2012 |
| KR | 210-2013-0052119 | 5/2013 |
| KR | 10-2013-0095024 | 8/2013 |
| KR | 20230024816 | 2/2023 |
| KR | 20230115452 | 8/2023 |
| KR | 20230123537 | 8/2023 |
| KR | 102584559 | 10/2023 |
| KR | 102587103 | 10/2023 |
| WO | WO 92/21332 A1 | 12/1992 |
| WO | WO9309881 | 5/1993 |
| WO | WO 2000/050111 A | 8/2000 |
| WO | WO 2002/055131 A2 | 7/2002 |
| WO | WO 02094342 A2 | 11/2002 |
| WO | WO 2003/055486 A | 7/2003 |
| WO | WO 2003/0101454 A | 12/2003 |
| WO | WO 2007/083088 A1 | 7/2007 |
| WO | WO 2008/076717 A1 | 6/2008 |
| WO | WO 2009/096346 A1 | 8/2009 |
| WO | WO 2012/062600 A1 | 5/2012 |
| WO | WO 2012/138835 A2 | 10/2012 |
| WO | WO 2013/028934 A1 | 2/2013 |
| WO | WO 2014/182736 A1 | 11/2014 |
| WO | WO 2015/128499 A1 | 3/2015 |
| WO | WO2015/084544 A1 | 6/2015 |
| WO | WO 2015/115006 A1 | 8/2015 |
| WO | WO 2016/010864 A1 | 1/2016 |
| WO | WO 2016/116386 | 7/2016 |
| WO | WO 2016/118941 A1 | 7/2016 |
| WO | WO 2016/175720 A1 | 11/2016 |
| WO | WO 2016/196915 A1 | 12/2016 |
| WO | WO 2017/076590 A1 | 5/2017 |
| WO | WO 2017/108268 A1 | 6/2017 |
| WO | WO 2017/143515 A1 | 8/2017 |
| WO | WO 2017/177159 A3 | 10/2017 |
| WO | WO 2017/197704 A1 | 11/2017 |
| WO | WO 2017/205692 | 11/2017 |
| WO | WO 2017/206022 A1 | 12/2017 |
| WO | WO 2017/206212 A1 | 12/2017 |
| WO | WO 2017/215221 A1 | 12/2017 |
| WO | WO 2018/000761 A1 | 1/2018 |
| WO | WO 2018/000829 A1 | 1/2018 |
| WO | WO 2018/023920 A1 | 2/2018 |
| WO | WO2018/027189 A2 | 2/2018 |
| WO | WO 2018/032672 A1 | 2/2018 |
| WO | WO 2018/040380 A1 | 3/2018 |
| WO | WO 2018/041106 A1 | 3/2018 |
| WO | WO 2018/058884 A1 | 4/2018 |
| WO | WO 2018/111843 | 6/2018 |
| WO | WO 2018/113669 A1 | 6/2018 |
| WO | WO 2018/115781 A1 | 6/2018 |
| WO | WO 2018/163366 A1 | 9/2018 |
| WO | WO 2018/167066 | 9/2018 |
| WO | WO 2018/188616 A1 | 10/2018 |
| WO | WO 2018/188638 A1 | 10/2018 |
| WO | WO 2018/211252 A1 | 11/2018 |
| WO | WO 2018/220586 A2 | 12/2018 |
| WO | WO2018/220599 A1 | 12/2018 |
| WO | WO 2019/016681 | 1/2019 |
| WO | WO 2019/048749 A1 | 3/2019 |
| WO | WO 2019/052506 A1 | 3/2019 |
| WO | WO 2019/052574 A1 | 3/2019 |
| WO | WO 2019/069160 A1 | 4/2019 |
| WO | WO 2019/138076 A1 | 7/2019 |
| WO | WO 2019/173923 | 9/2019 |
| WO | WO 2019/198688 | 10/2019 |
| WO | WO 2019/211324 | 11/2019 |
| WO | WO 2019/238064 | 12/2019 |
| WO | WO 2019/242746 A1 | 12/2019 |
| WO | WO 2020/019030 A1 | 1/2020 |
| WO | WO 2020/048437 A1 | 3/2020 |
| WO | WO 2020/057636 A2 | 3/2020 |
| WO | WO2020187138 A1 | 9/2020 |
| WO | WO 2020/225534 A1 | 11/2020 |
| WO | WO 2020/254862 A1 | 12/2020 |
| WO | WO 2021/036827 A1 | 3/2021 |
| WO | WO2022/104246 | 5/2022 |
| WO | WO2022/200151 | 9/2022 |
| WO | WO2022/203187 | 9/2022 |
| WO | WO 2023/018059 | 2/2023 |
| WO | WO2023/143058 | 8/2023 |
| WO | WO2023/179691 | 9/2023 |
| WO | WO2023/249371 | 12/2023 |

OTHER PUBLICATIONS

English machine translation of CN-2648836-Y; Han; Oct. 20, 2004, 21 pages. (Year: 2004).*
English machine translation of CN 104082853 A; Yin; Oct. 8, 2014; 9 pages. (Year: 2014).*
Extended European Search Report mailed May 8, 2023 for co-pending European Application No. 19956956.7, 9 pages.
Office Action, co-pending KR Application No. 10-2022-7024457 dated Dec. 22, 2023; 10 pages (with English translation).
ISR and Written Opinion mailed Mar. 10, 2022 for Intl. Appl. No. PCT/GB2021053312.
ISR and Written Opinion mailed Mar. 10, 2022 for Intl. Appl. No. PCT/GB2021053311.
ISR and Written Opinion mailed Mar. 10, 2022 for Intl. Appl. No. PCT/GB2021053316.
UKIPO Search Report dated Nov. 24, 2021 for Application No. GB2111261.0.
UKIPO Search Report dated Nov. 24, 2021 for Application No. GB2113658.5.
UKIPO Search Report dated Nov. 24, 2021 for Application No. GB2113623.9.
EPO Search Report dated Nov. 12, 2021 for corresponding European Application No. 19870060.1.
EPO Search Report dated Oct. 27, 2021 for corresponding European Application No. 19870058.5.
International Search Report and Written Opinion for International Appl. No. PCT/GB2021/050842 mailed Jul. 5, 2021.
International Search Report and Written Opinion for International Appl. No. PCT/GB2021/050817 mailed Jun. 17, 2021.
UKIPO Search Report for UK Appl. No. GB2104872.3 dated Jun. 25, 2021.
EPO Search Report and Search Opinion for International Appl. No. PCT/IB2019/060812 dated Jun. 22, 2021.
Extended European Search Report and Search Opinion for corresponding EP Application No. 20214228.7 dated May 26, 2021.
International Search Report and Written Opinion for International Appl. No. PCT/IB2019/055192 dated Apr. 29, 2020.
International Search Report for corresponding PCT Application No. PCT/GB2020/053219 mailed Mar. 31, 2021.
Written Opinion mailed Nov. 10, 2020 for corresponding International Application No. PCT/IB2019/060812.
International Search Report mailed Nov. 10, 2020 for corresponding International Application No. PCT/IB2019/060812.
EPO Search Report mailed Nov. 9, 2020 for corresponding EPO Application No. 19870059.3 (PCT/IB2019/060808).
Written Opinion mailed Oct. 20, 2020 for corresponding International Application No. PCT/IB2019/060811.
International Search Report mailed Oct. 20, 2020 for corresponding International Application No. PCT/IB2019/060811.
Written Opinion mailed Oct. 19, 2020 for corresponding International Application No. PCT/IB2019/060810.
International Search Report mailed Oct. 19, 2020 for corresponding International Application No. PCT/IB2019/060810.

(56) References Cited

OTHER PUBLICATIONS

EPO Search Report dated Sep. 16, 2020 for corresponding EPO U.S. Appl. No. 20/168,231.
Extended EPO Search Report mailed Sep. 15, 2020 for corresponding EPO Application No. 20168938.7.
Written Opinion mailed Jun. 25, 2020 for corresponding International Application No. PCT/IB2019/060808.
International Search Report mailed Jun. 25, 2020 for corresponding International Application No. PCT/IB2019/060808.
Written Opinion mailed Apr. 29, 2020 for corresponding International Application No. PCT/IB2019/055192.
International Search Report mailed Apr. 29, 2020 for corresponding International Application No. PCT/IB2019/055192.
EPO search report dated Sep. 20, 2017 for corresponding EPO Application No. 20168245.7.
EPO Supplementary Search Report for EPO Application No. EP 3 278 678 A4 dated Oct. 4, 2018.
International Search Report for International Appl. No. WO 2017/177159 A3 mailed Sep. 26, 2017.
EPO Supplementary Search Report for EPO Application No. EP 1 618 803 A4 dated Jul. 27, 2007.
ISR and Written Opinion mailed Nov. 4, 2020 for International Application No. PCT/IB2019/060806.
ISR and Written Opinion mailed Nov. 4, 2020 for International Application No. PCT/IB2019/060807.
ISR and Written Opinion mailed Oct. 20, 2020 for International Application No. PCT/IB2019/060809.
Official Notice of Rejection, JP Application No. 2022-561689 mailed Oct. 3, 2023 (with English translation); 8 pages.
Intention to Grant dated Jul. 11, 2024 for co-pending European Application No. 19956340.4; 32 pages.
Akira Kubo, Part 1: What is Personal Authentication ?—The Last Resort for Internet Security-Series: Re-Introduction to PKI, Japan, @IT, Apr. 5, 2003; https://atmarkit.itmedia.co.jp/fsecurity/rensai/re_pki01/re_pki01.html (newly cited reference showing well-known technique) (No English version).

\* cited by examiner

ULTRASONIC MIST INHALER

This application is a National Phase Application under 35 U.S.C. § 371 of PCT/IB2019/060807, filed Dec. 15, 2019 (published on Jun. 24, 2021 as WO 2021/123866 A1) the entire contents of which are incorporated herein by reference.

FIELD OF THE DISCLOSED TECHNOLOGY

The invention relates to an ultrasonic mist inhaler for atomizing a liquid by ultrasonic vibrations.

BACKGROUND

Electronic vaporizing inhalers are becoming popular among smokers who also want to avoid the tar and other harsh chemicals associated with traditional cigarettes and who wish to satisfy the craving for nicotine. Electronic vaporizing inhalers may contain liquid nicotine, which is typically a mixture of nicotine oil, a solvent, water, and often flavoring. When the user draws, or inhales, on the electronic vaporizing inhaler, the liquid nicotine is drawn into a vaporizer where it is heated into a vapor. As the user draws on the electronic vaporizing inhaler, the vapor containing the nicotine is inhaled. Such electronic vaporizing inhalers may have medical purpose.

Electronic vaporizing inhalers and other vapor inhalers typically have similar designs. Most electronic vaporizing inhalers feature a liquid nicotine reservoir with an interior membrane, such as a capillary element, typically cotton, that holds the liquid nicotine so as to prevent leaking from the reservoir. Nevertheless, these cigarettes are still prone to leaking because there is no obstacle to prevent the liquid from flowing out of the membrane and into the mouthpiece. A leaking electronic vaporizing inhaler is problematic for several reasons. As a first disadvantage, the liquid can leak into the electronic components, which can cause serious damage to the device. As a second disadvantage, the liquid can leak into the electronic vaporizing inhaler mouthpiece, and the user may inhale the unvaporized liquid.

Electronic vaporizing inhalers are also known for providing inconsistent doses between draws. The aforementioned leaking is one cause of inconsistent doses because the membrane may be oversaturated or undersaturated near the vaporizer. If the membrane is oversaturated, then the user may experience a stronger than desired dose of vapor, and if the membrane is undersaturated, then the user may experience a weaker than desired dose of vapor. Additionally, small changes in the strength of the user's draw may provide stronger or weaker doses. Inconsistent dosing, along with leaking, can lead to faster consumption of the vaping liquid.

Additionally, conventional electronic vaporizing inhalers tend to rely on inducing high temperatures of a metal heating component configured to heat a liquid in the e-cigarette, thus vaporizing the liquid that can be breathed in. Problems with conventional electronic vaporizing inhalers may include the possibility of burning metal and subsequent breathing in of the metal along with the burnt liquid. In addition, some may not prefer the burnt smell caused by the heated liquid.

Electronic vaporizing inhalers are generally designed so that the liquid nicotine reservoir is arranged away from the metal heating component to prevent heating the unused liquid in the reservoir. This arrangement makes the inhaler device cumbersome and more complex to produce.

Thus, a need exists in the art for an electronic vaporizing inhaler that is better able to withstand these disadvantages.

BRIEF SUMMARY

According to one aspect of the invention, an ultrasonic mist inhaler, comprises:
 a mouthpiece for inhaling the mist,
 a liquid reservoir structure comprising a liquid chamber adapted to receive liquid to be atomized,
 a sonication chamber in fluid communication with the liquid chamber,
 wherein at least part of the liquid reservoir structure and the mouthpiece form the sonication chamber.

The arrangement of the mouthpiece with the sonication chamber renders the ultrasonic mist inhaler more compact.

Using a sonication chamber for ultrasonic vibrations in an ultrasonic mist inhaler allows the combination of the liquid chamber and the sonication chamber into the liquid reservoir structure.

It is noted that the expression "mist" used in the invention means the liquid is not heated as usually in traditional inhalers known from the prior art. In fact, traditional inhalers use heating elements to heat the liquid above its boiling temperature to produce a vapor, which is different from a mist.

In fact, when sonicating liquids at high intensities, the sound waves that propagate into the liquid media result in alternating high-pressure (compression) and low-pressure (rarefaction) cycles, at different rates depending on the frequency. During the low-pressure cycle, high-intensity ultrasonic waves create small vacuum bubbles or voids in the liquid. When the bubbles attain a volume at which they can no longer absorb energy, they collapse violently during a high-pressure cycle. This phenomenon is termed cavitation. During the implosion very high pressures are reached locally. At cavitation, broken capillary waves are generated, and tiny droplets break the surface tension of the liquid and are quickly released into the air, taking mist form.

In the ultrasonic mist inhaler, the liquid reservoir structure may comprise an inhalation channel providing an air passage from the sonication chamber toward the surroundings.

In the ultrasonic mist inhaler, the inhalation channel may comprise a frustoconical element arranged between the mouthpiece and the liquid reservoir structure.

In the ultrasonic mist inhaler, the inhalation channel may comprise an inner container delimiting the sonication chamber and the liquid chamber.

In the ultrasonic mist inhaler, the inner container may form the inner wall of the liquid chamber.

In the ultrasonic mist inhaler, the frustoconical element may be in contact with the inner container.

In the ultrasonic mist inhaler, the mouthpiece may comprise an inner duct receiving the frustoconical element.

In the ultrasonic mist inhaler, the liquid reservoir structure may comprise an outer container delimiting the outer wall of the liquid chamber.

In the ultrasonic mist inhaler, a capillary element may be arranged between the liquid chamber and the sonication chamber.

In the ultrasonic mist inhaler, the inner container may comprise a first section and a second section between which the capillary element is arranged.

The capillary element may be a gauze. The capillary element may be formed of bamboo fibers, preferably in 100% bamboo fibers, or cotton, silica, tobacco cotton, or any combination of such material.

In the ultrasonic mist inhaler, the capillary element may have a flat shape extending from the sonication chamber to the liquid chamber.

In the ultrasonic mist inhaler, the capillary element may comprise a central portion and a peripheral portion.

In the ultrasonic mist inhaler, the peripheral portion may have an L-shape cross section extending down to the liquid chamber.

In the ultrasonic mist inhaler, the central portion may have a U-shape cross section extending down to the sonication chamber.

In the ultrasonic mist inhaler, the liquid reservoir structure may comprise an airflow member for providing air flow from the surroundings to the sonication chamber.

In the ultrasonic mist inhaler, the airflow member may comprise an airflow bridge and an airflow duct, the airflow bridge having at least an airway opening forming a portion of the inhalation channel and the airflow duct extending in the sonication chamber from the airflow bridge for providing the air flow from the surroundings to the sonication chamber.

Preferably, the airflow bridge comprises two semicircular airway openings.

Preferably, the airflow bridge is engaged with the frustoconical element.

In the ultrasonic mist inhaler, the airflow duct may face the capillary element.

In the ultrasonic mist inhaler, the airflow bridge may comprise at least a peripheral opening providing air flow to the airflow duct.

In the ultrasonic mist inhaler, the frustoconical element may comprise at least a peripheral opening aligned with the peripheral opening of the airflow bridge.

In the ultrasonic mist inhaler, the mouthpiece may comprise at least a peripheral opening aligned with the peripheral opening of the airflow bridge and the peripheral opening of the frustoconical element.

In the ultrasonic mist inhaler, an airflow chamber may be arranged between the mouthpiece and the frustoconical element.

More precisely, the end of the airflow duct may extend in the sonication chamber and is close to or at the capillary element.

In the ultrasonic mist inhaler, the airflow bridge and the airflow duct may be made in one piece.

In the ultrasonic mist inhaler, the sonication chamber may comprise means of ultrasonic vibrations.

The expression "means of ultrasonic vibrations" is similar to the expression "ultrasonic oscillation component" used in the patent application PCT/IB2019/055192.

In the ultrasonic mist inhaler, the means of ultrasonic vibrations are supported by an elastic member.

The elastic member is formed from an annular plate-shaped rubber.

The elastic member has an inner hole wherein a groove is designed for maintaining the means of ultrasonic vibrations.

In this case, since the elastic member is in line contact with the means of ultrasonic vibrations, suppression of vibrations of the liquid reservoir structure can more effectively be prevented. Thus, fine particles of the liquid atomized by the atomizing member can be sprayed farther.

In the ultrasonic mist inhaler, a high-frequency voltage may be applied to the means of ultrasonic vibrations to ultrasonically vibrate the means of ultrasonic vibrations, whereby a liquid supplied to a portion of the means of ultrasonic vibrations can be atomized and sprayed.

According to the ultrasonic mist inhaler, fine particles of the liquid atomized by the means of ultrasonic vibrations having a relatively small size can be sprayed farther.

Such means of ultrasonic vibrations may be a transducer, preferably designed in a circular plate-shape. The material of the piezoelectric transducer is preferably in ceramic.

In the ultrasonic mist inhaler, the U-shape cross section may have an inner portion and an outer portion, the inner portion of the U-shape cross section being in surface contact with the means of ultrasonic vibrations and the outer portion of the U-shape cross section being not in surface contact with the means of ultrasonic vibrations.

In the ultrasonic mist inhaler, the outer portion of the U-shape cross section may have airflow apertures through which may pass the mist produced between the outer portion of the U-shape cross section and the means of ultrasonic vibrations.

In the ultrasonic mist inhaler, the inner container may be configured to receive a mechanical spring.

Preferably, the mechanical spring pushes the central portion of the capillary element onto the means of ultrasonic vibrations to ensure the surface contact.

In the ultrasonic mist inhaler, the sonication chamber may have a bottom plate closing the sonication chamber.

In the ultrasonic mist inhaler, the bottom plate may be configured to support the elastic member.

In the ultrasonic mist inhaler, the bottom plate may comprise an upper surface having a recess wherein the elastic member is received.

In the ultrasonic mist inhaler, the liquid chamber may comprise a top surface representing the maximum level of the liquid chamber and the bottom surface representing the minimum level of the liquid, and wherein the bottom surface being the upper surface of the bottom plate.

In the ultrasonic mist inhaler, the liquid reservoir structure may comprise a cap closing the liquid chamber.

In the ultrasonic mist inhaler, the cap may comprise a lower surface, the top surface of the liquid chamber being the lower surface of the cap.

In the ultrasonic mist inhaler, the bottom plate may be arranged to receive connectors for powering the means of ultrasonic vibrations.

In the ultrasonic mist inhaler, a first connector and a second connector, the first connector is a spring-loaded contact probe and the second connector is a side pin crossing the elastic member. A spring-loaded contact probe provides a permanent contact with the means of ultrasonic vibrations.

Preferably, a metal plate ensures electrical contact between the second connector and the means of ultrasonic vibrations.

In the ultrasonic mist inhaler, the liquid reservoir structure may have a top end comprising an airway fluidically coupled to the internal bore and configured to allow liquid mist to flow out of the airway.

In the ultrasonic mist inhaler, the liquid reservoir structure may be arranged between a mouthpiece and a casing housing electrical components for powering and operating the inhaler.

The bottom plate is sealed, thus preventing leakage of liquid from the sonication chamber to the casing.

In the ultrasonic mist inhaler, the top end of the liquid reservoir structure may be coupled with the mouthpiece via the frustoconical element, the mouthpiece being configured to allow suction of liquid mist flowing out of the airway to the surroundings.

Advantageously, the liquid reservoir structure is detachable from the mouthpiece and the casing.

The liquid reservoir structure and the mouthpiece or the casing may include complimentary arrangements for engaging with one another; further such complimentary arrangements may include; a bayonet type arrangement; a threaded engaged type arrangement; a magnetic arrangement; and, a friction fit arrangement; wherein the liquid reservoir structure includes a portion of the arrangement and the mouthpiece or the casing includes the complimentary portion of the arrangement.

Such design permits the liquid reservoir structure to be disposable. The liquid reservoir structure may be removed and reinstalled when required; a feature that gives the user the freedom to interchange flavors without the limitation of either completely using or having to discard unused liquid.

Further, such design eliminates the risk of fatigue of the means of ultrasonic vibrations in the sonication chamber and has a disposable means of ultrasonic vibrations which prevents the risk of fatigue and a disposable capillary element which prevents the risk of mixing flavor.

In the ultrasonic mist inhaler, an integrated circuit may be coupled to the bottom end of the liquid reservoir structure and communicatively coupled to the means of ultrasonic vibrations, the integrated circuit configured to cause the means of ultrasonic vibrations to vibrate.

Preferably, the means of ultrasonic vibrations is in electrical communication with an integrated circuit, preferably via the connectors.

Advantageously, the integrated circuit is designed to convert a direct current into an alternate current at high frequency.

The means of ultrasonic vibrations may be powered from electrical components of the casing through the connectors.

Preferably, the casing is configured to contain an electrical storage device and may encase at least a portion of the integrated circuit.

The casing may have all features described in the patent application PCT/IB2019/055192.

The ultrasonic mist inhaler according to the invention, wherein said liquid to be received in the liquid chamber comprises 57-70% (w/w) vegetable glycerin and 30-43% (w/w) propylene glycol, said propylene glycol including nicotine and flavorings.

An ultrasonic mist inhaler or a personal ultrasonic atomizer device, comprising:
a liquid reservoir structure comprising a liquid chamber or cartridge adapted to receive liquid to be atomized,
a sonication chamber in fluid communication with the liquid chamber or cartridge,
wherein said liquid to be received in the liquid chamber comprises 57-70% (w/w) vegetable glycerin and 30-43% (w/w) propylene glycol, said propylene glycol including nicotine and flavorings.

BRIEF DESCRIPTION OF THE DRAWINGS

Some embodiments are illustrated by way of example and not limitation in the figures of the accompanying drawings.

DETAILED DESCRIPTION

The foregoing summary, as well as the following detailed description of certain embodiments of the present invention, will be better understood when read in conjunction with the appended drawings.

As used herein, an element recited in the singular and preceded with the word "a" or "an" should be understood as not excluding plural of said elements, unless such exclusion is explicitly stated. Furthermore, the references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The present invention is directed to an ultrasonic mist inhaler. The description of the invention and accompanying figures will be directed to the electronic vaporizing inhaler embodiment; however, other embodiments are envisioned, such as an inhaler for hookah, flavored liquids, medicine, and herbal supplements. Additionally, the device can be packaged to look like an object other than a cigarette. For instance, the device could resemble another smoking instrument, such as a pipe, water pipe, or slide, or the device could resemble another non-smoking related object.

Ultrasonic mist inhalers are either disposable or reusable. The term "reusable" as used herein implies that the energy storage device is rechargeable or replaceable or that the liquid is able to be replenished either through refilling or through replacement of the liquid reservoir structure. Alternatively, in some embodiments reusable electronic device is both rechargeable and the liquid can be replenished. A disposable embodiment will be described first, followed by a description of a reusable embodiment.

Conventional electronic vaporizing inhaler tend to rely on inducing high temperatures of a metal component configured to heat a liquid in the inhaler, thus vaporizing the liquid that can be breathed in. The liquid typically contains nicotine and flavorings blended into a solution of propylene glycol (PG) and vegetable glycerin (VG), which is vaporized via a heating component at high temperatures. Problems with conventional inhaler may include the possibility of burning metal and subsequent breathing in of the metal along with the burnt liquid. In addition, some may not prefer the burnt smell or taste caused by the heated liquid.

In contrast, aspects of the present disclosure include an ultrasonic mist inhaler that atomizes the liquid through ultrasonic vibrations, which produces micro water bubbles in the liquid. When the bubbles come into contact with ambient air molecules, water droplets of about 0.25 to 0.5 microns spray into the air, thereby generating micro-droplets that can be absorbed through breathing, similar to breathing in a mist.

No heating elements are involved, thereby leading to no burnt elements and reducing second-hand smoke effects.

Figure 1:
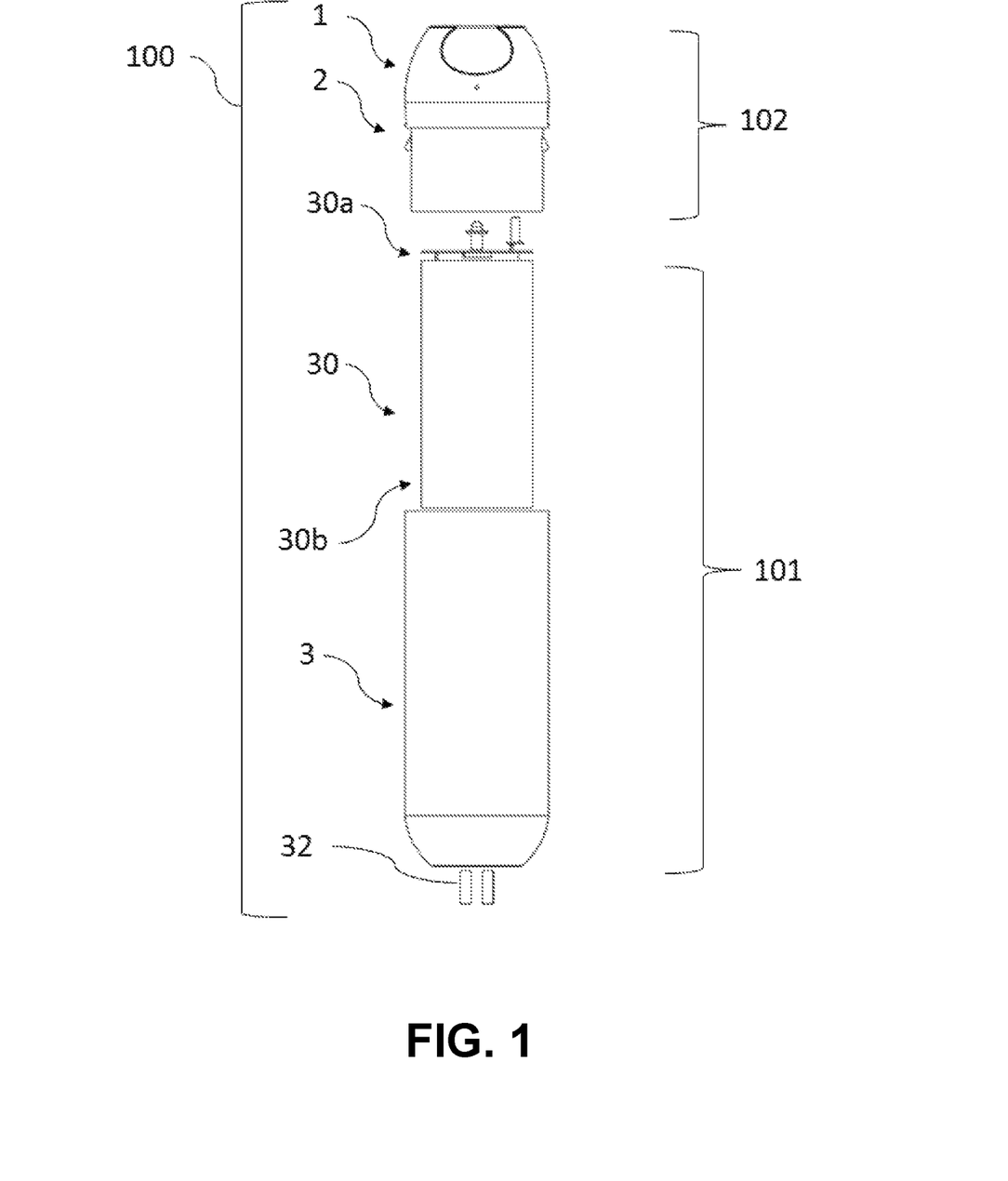
FIG. 1 is an exploded view of components of the ultrasonic mist inhaler according to an embodiment of the invention.

FIG. 1 depicts a disposable ultrasonic mist inhaler embodiment 100 of the invention. As can be seen in FIG. 1, the ultrasonic mist inhaler 100 has a cylindrical body with a relatively long length as compared to the diameter. In terms of shape and appearance, the ultrasonic mist inhaler 100 is designed to mimic the look of a typical cigarette. For instance, the inhaler can feature a first portion 101 that primarily simulates the tobacco rod portion of a cigarette and a second portion 102 that primarily simulates a filter. In the disposable embodiment of the invented device, the first portion and second portion are regions of a single, but-separable device. The designation of a first portion 101 and a second portion 102 is used to conveniently differentiate the components that are primarily contained in each portion.

As can be seen in FIG. 1, the ultrasonic mist inhaler comprises a mouthpiece 1, a liquid reservoir structure 2 and a casing 3. The first portion 101 comprises the casing 3 and the second portion 102 comprises the mouthpiece 1 and the reservoir structure 2.

The first portion 101 contains the power supply energy.

An electrical storage device 30 powers the ultrasonic mist inhaler 100. The electrical storage device 30 can be a battery, including but not limited to a lithium-ion, alkaline, zinc-carbon, nickel-metal hydride, or nickel-cadmium battery; a super capacitor; or a combination thereof. In the disposable embodiment, the electrical storage device 30 is not rechargeable, but, in the reusable embodiment, the electrical storage device 30 would be selected for its ability to recharge. In the disposable embodiment, the electrical storage device 30 is primarily selected to deliver a constant voltage over the life of the inhaler 100. Otherwise, the performance of the inhaler would degrade over time. Preferred electrical storage devices that are able to provide a consistent voltage output over the life of the device include lithium-ion and lithium polymer batteries.

The electrical storage device 30 has a first end 30a that generally corresponds to a positive terminal and a second end 30b that generally corresponds to a negative terminal. The negative terminal is extending to the first end 30a.

Because the electrical storage device 30 is located in the first portion 101 and the liquid reservoir structure 2 is located in the second portion 102, the joint needs to provide electrical communication between those components. In the present invention, electrical communication is established using at least an electrode or probe that is compressed together when the first portion 101 is tightened into the second portion 102.

In order for this embodiment to be reusable, the electrical storage device 30 is rechargeable. The casing 3 contains a charging port 32.

The integrated circuit 4 has a proximal end 4a and a distal end 4b. The positive terminal at the first end 30a of the electrical storage device 30 is in electrical communication with a positive lead of the flexible integrated circuit 4. The negative terminal at the second end 30b of the electrical storage device 30 is in electrical communication with a negative lead of the integrated circuit 4. The distal end 4b of the integrated circuit 4 comprise a microprocessor. The microprocessor is configured to process data from a sensor, to control a light, to direct current flow to means of ultrasonic vibrations 5 in the second portion 102, and to terminate current flow after a preprogrammed amount of time.

The sensor detects when the ultrasonic mist inhaler 100 is in use (when the user draws on the inhaler) and activates the microprocessor. The sensor can be selected to detect changes in pressure, air flow, or vibration. In a preferred embodiment, the sensor is a pressure sensor. In the digital embodiment, the sensor takes continuous readings which in turn requires the digital sensor to continuously draw current, but the amount is small and overall battery life would be negligibly affected.

Additionally, the integrated circuit 4 may comprise a H bridge, preferably formed by 4 MOSFETs to convert a direct current into an alternate current at high frequency.

Figure 2:
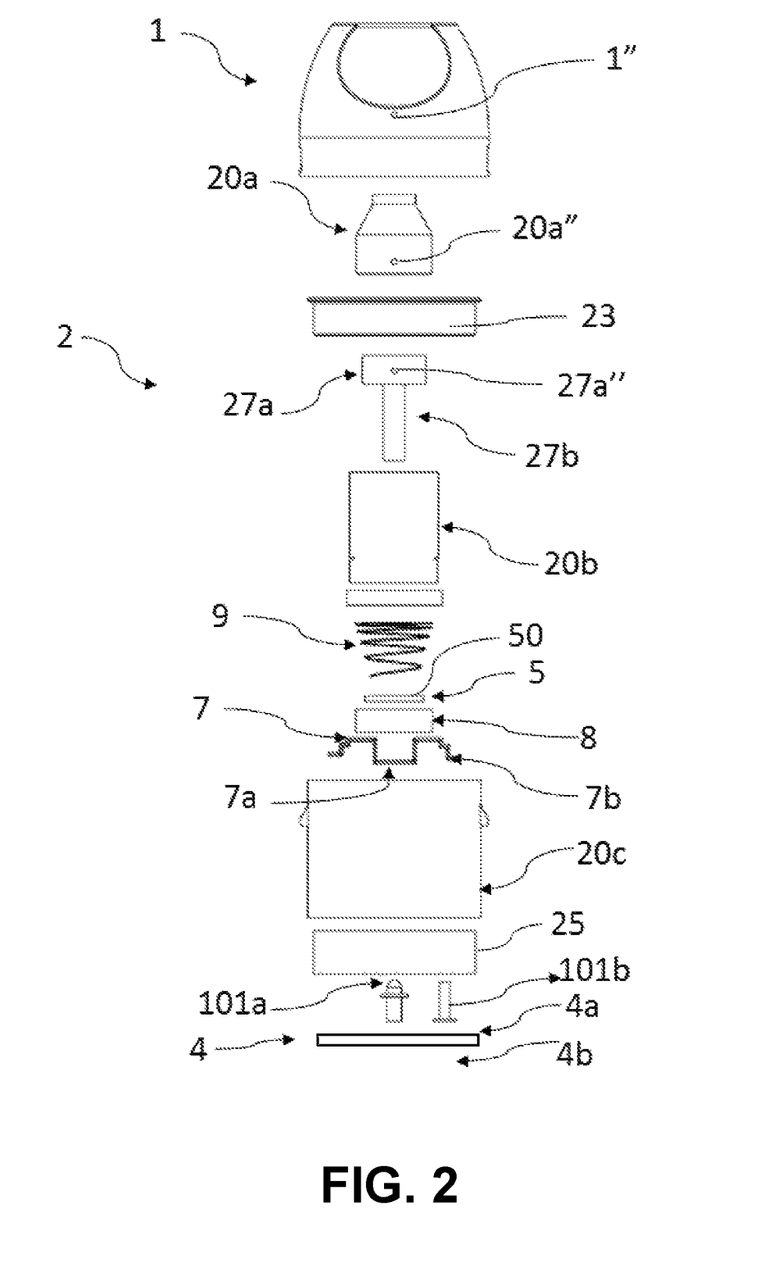
FIG. 2 is an exploded view of components of the inhaler liquid reservoir structure according to an embodiment of the invention.
Figure 3:
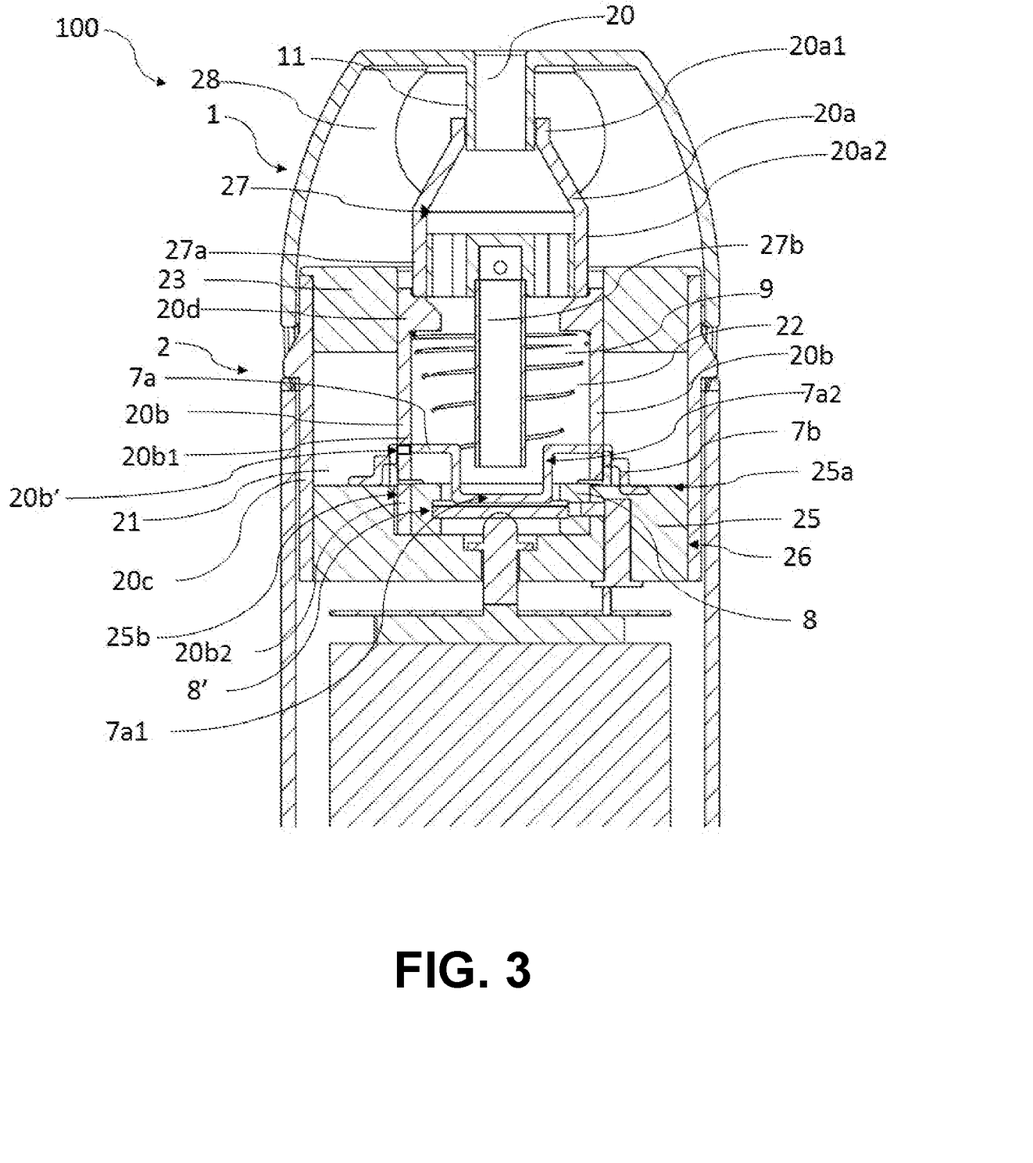
FIG. 3 is a cross-section view of components of the inhaler liquid reservoir structure according to FIG. 1.

Referring to FIG. 2 and FIG. 3, illustrations of a liquid reservoir structure 2 according to an embodiment are shown. The liquid reservoir structure 2 comprises a liquid chamber 21 adapted to receive liquid to be atomized and a sonication chamber 22 in fluid communication with the liquid chamber 21.

In the embodiment shown, the liquid reservoir structure 2 comprises an inhalation channel 20 providing an air passage from the sonication chamber 22 toward the surroundings.

As an example of sensor position, the sensor may be located in the sonication chamber 22.

The inhalation channel 20 has a frustoconical element 20a and an inner container 20b.

Figure 4A:
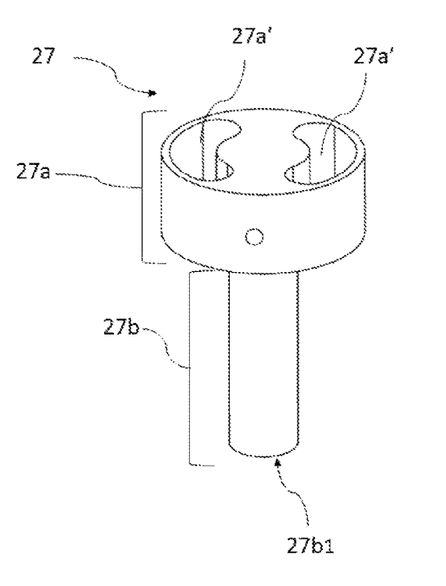
FIG. 4A is an isometric view of an airflow member of the inhaler liquid reservoir structure according to FIGS. 2 and 3.
Figure 4B:
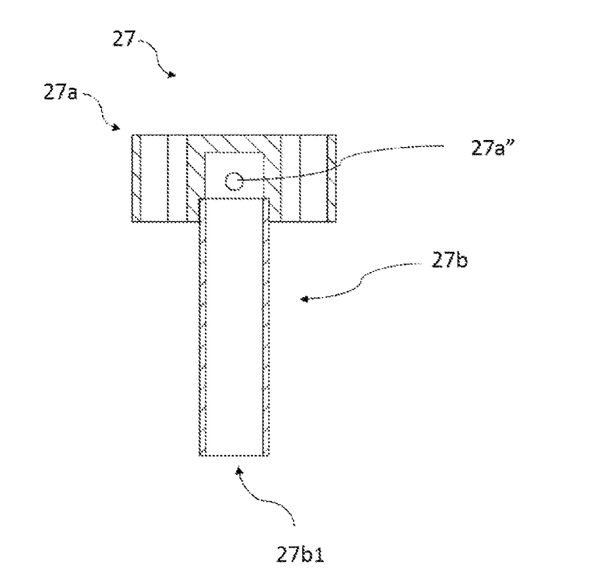
FIG. 4B is a cross-section view of the airflow member shown in FIG. 4A.

As depicted in FIGS. 4A and 4B, further the inhalation channel 20 has an airflow member 27 for providing air flow from the surroundings to the sonication chamber 22.

The airflow member 27 has an airflow bridge 27a and an airflow duct 27b made in one piece, the airflow bridge 27a having two airway openings 27a' forming a portion of the inhalation channel 20 and the airflow duct 27b extending in the sonication chamber 22 from the airflow bridge 27a for providing the air flow from the surroundings to the sonication chamber.

The airflow bridge 27a cooperates with the frustoconical element 20a at the second diameter 20a2.

The airflow bridge 27a has two opposite peripheral openings 27a" providing air flow to the airflow duct 27b.

The cooperation with the airflow bridge 27a and the frustoconical element 20a is arranged so that the two opposite peripheral openings 27a" cooperate with complementary openings 20a" in the frustoconical element 20a.

The mouthpiece 1 and the frustoconical element 20a are radially spaced and an airflow chamber 28 is arranged between them.

As depicted in FIGS. 1 and 2, the mouthpiece 1 has two opposite peripheral openings 1".

The peripheral openings 27a", 20a", 1" of the airflow bridge 27a, the frustoconical element 20a and the mouthpiece 1 directly supply maximum air flow to the sonication chamber 22.

The frustoconical element 20a includes an internal passage, aligned in the similar direction as the inhalation channel 20, having a first diameter 20a1 less than that of a second diameter 20a2, such that the internal passage reduces in diameter over the frustoconical element 20a.

The frustoconical element 20a is positioned in alignment with the means of ultrasonic vibrations 5 and a capillary element 7, wherein the first diameter 20a1 is linked to an inner duct 11 of the mouthpiece 1 and the second diameter 20a2 is linked to the inner container 20b.

The inner container 20b has an inner wall delimiting the sonication chamber 22 and the liquid chamber 21.

The liquid reservoir structure 2 has an outer container 20c delimiting the outer wall of the liquid chamber 21.

The inner container 20b and the outer container 20c are respectively the inner wall and the outer wall of the liquid chamber 21.

The liquid reservoir structure 2 is arranged between the mouthpiece 1 and the casing 3 and is detachable from the mouthpiece 1 and the casing 3.

The liquid reservoir structure 2 and the mouthpiece 1 or the casing 3 may include complimentary arrangements for engaging with one another; further such complimentary arrangements may include one of the following: a bayonet type arrangement; a threaded engaged type arrangement; a magnetic arrangement; or a friction fit arrangement; wherein the liquid reservoir structure 2 includes a portion of the 
arrangement and the mouthpiece 1 or the casing 3 includes the complimentary portion of the arrangement.

In the reusable embodiment, the components are substantially the same. The differences in the reusable embodiment vis-a-vis the disposable embodiment are the accommodations made to replace the liquid reservoir structure 2.

As shown in FIG. 3, the liquid chamber 21 has a top wall 23 and a bottom wall 25 closing the inner container 20*b* and the outer container 20*c* of the liquid chamber 21.

The capillary element 7 is arranged between a first section 20*b*1 and a second section 20*b*2 of the inner container 20*b*.

The capillary element 7 has a flat shape extending from the sonication chamber to the liquid chamber.

As depicted in FIG. 2 or 3, the capillary element 7 comprises a central portion 7*a* in U-shape and a peripheral portion 7*b* in L-shape.

The L-shape portion 7*b* extends into the liquid chamber 21 on the inner container 20*b* and along the bottom wall 25.

The U-shape portion 7*a* is contained into the sonication chamber 21. The U-shape portion 7*a* on the inner container 20*b* and along the bottom wall 25.

In the ultrasonic mist inhaler, the U-shape portion 7*a* has an inner portion 7*a*1 and an outer portion 7*a*2, the inner portion 7*a*1 being in surface contact with an atomization surface 50 of the means of ultrasonic vibrations 5 and the outer portion 7*a*2 being not in surface contact with the means of ultrasonic vibrations 5.

The bottom wall 25 of the liquid chamber 21 is a bottom plate 25 closing the liquid chamber 21 and the sonication chamber 22. The bottom plate 25 is sealed, thus preventing leakage of liquid from the sonication chamber 22 to the casing 3.

The bottom plate 25 has an upper surface 25*a* having a recess 25*b* on which is inserted an elastic member 8. The means of ultrasonic vibrations 5 are supported by the elastic member 8. The elastic member 8 is formed from an annular plate-shaped rubber having an inner hole 8' wherein a groove is designed for maintaining the means of ultrasonic vibrations 5.

The top wall 23 of the liquid chamber 21 is a cap 23 closing the liquid chamber 23.

The top wall 23 has a top surface 23 representing the maximum level of the liquid that the liquid chamber 21 may contain and the bottom surface 25 representing the minimum level of the liquid in the liquid chamber 21.

The top wall 23 is sealed, thus preventing leakage of liquid from the liquid chamber 21 to the mouthpiece 1.

The top wall 23 and the bottom wall 25 are fixed to the liquid reservoir structure 2 by means of fixation such as screws, glue, or friction.

As depicted in FIG. 3, the elastic member is in line contact with the means of ultrasonic vibrations 5 and prevents contact between the means of ultrasonic vibrations 5 and the inhaler walls, suppression of vibrations of the liquid reservoir structure are more effectively prevented. Thus, fine particles of the liquid atomized by the atomizing member can be sprayed farther.

As depicted in FIG. 3, the inner container 20*b* has openings 20*b*' between the first section 20*b*1 and the second section 20*b*2 from which the capillary element 7 is extending from the sonication chamber 21. The capillary element 7 absorbs liquid from the liquid chamber 21 through the apertures 20*b*'. The capillary element 7 is a wick. The capillary element 7 transports liquid to the sonication chamber 22 via capillary action. Preferably the capillary element 7 is made of bamboo fibers; however, cotton, paper, or other fiber strands could be used for a wick material.

In one embodiment of the ultrasonic mist inhaler 100, as can be seen in FIG. 3, the means of ultrasonic vibrations 5 are disposed directly below the capillary element 7.

The means of ultrasonic vibrations 5 may be a transducer. For example, the means of ultrasonic vibrations 5 may be a piezoelectric transducer, preferably designed in a circular plate-shape. The material of the piezoelectric transducer is preferably in ceramic.

A variety of transducer materials can also be used for the means of ultrasonic vibrations 5.

The end of the airflow duct 27*b*1 faces the means of ultrasonic vibrations 5. The means of ultrasonic vibrations 5 are in electrical communication with electrical contactors 101*a*, 101*b*. It is noted that, the distal end 4*b* of the integrated circuit 4 has an inner electrode and an outer electrode. The inner electrode contacts the first electrical contact 101*a* which is a spring contact probe, and the outer electrode contacts the second electrical contact 101*b* which is a side pin. Via the integrated circuit 4, the first electrical contact 101*a* is in electrical communication with the positive terminal of the electrical storage device 30 by way of the microprocessor, while the second electrical contact 101*b* is in electrical communication with the negative terminal of the electrical storage device 30.

The electrical contacts 101*a*, 101*b* crossed the bottom plate 25. The bottom plate 25 is designed to be received inside the perimeter wall 26 of the liquid reservoir structure 2. The bottom plate 25 rests on complementary ridges, thereby creating the liquid chamber 21 and sonication chamber 22.

The inner container 20*b* comprises a circular inner slot 20*d* on which a mechanical spring is applied.

By pushing the central portion 7*a*1 onto the means of ultrasonic vibrations 5, the mechanical spring 9 ensures a contact surface between them.

The liquid reservoir structure 2 and the bottom plate 25 can be made using a variety of thermoplastic materials.

When the user draws on the ultrasonic mist inhaler 100, an air flow is drawn from the peripheral openings 1'' and penetrates the airflow chamber 28, passes the peripheral openings 27*a*'' of the airflow bridge 27*a* and the frustoconical element 20*a* and flows down into the sonication chamber 22 via the airflow duct 27*b* directly onto the capillary element 7. At the same time, the liquid is drawn from the reservoir chamber 21 by capillarity, through the plurality of apertures 20*b*', and into the capillary element 7. The capillary element 7 brings the liquid into contact with the means of ultrasonic vibrations 5 of the inhaler 100. The user's draw also causes the pressure sensor to activate the integrated circuit 4, which directs current to the means of ultrasonic vibrations 5. Thus, when the user draws on the mouthpiece 1 of the inhaler 100, two actions happen at the same time. Firstly, the sensor activates the integrated circuit 4, which triggers the means of ultrasonic vibrations 5 to begin vibrating. Secondly, the draw reduces the pressure outside the reservoir chamber 21 such that flow of the liquid through the apertures 20*b*' begins, which saturates the capillary element 7. The capillary element 7 transports the liquid to the means of ultrasonic vibrations 5, which causes bubbles to form in a capillary channel by the means of ultrasonic vibrations 5 and mist the liquid. Then, the mist liquid is drawn by the user.

The ultrasonic mist inhaler 100 of the present disclosures is a more powerful version of current portable medical nebulizers, in the shape and size of current e-cigarettes and with a particular structure for effective vaporization. It is a healthier alternative to cigarettes and current e-cigarettes products.

The ultrasonic mist inhaler 100 of the present disclosures has particular applicability for those who use electronic inhalers as a means to quit smoking and reduce their nicotine dependency. The ultrasonic mist inhaler 100 provides a way to gradually taper the dose of nicotine.

Other embodiments of the invented ultrasonic mist inhaler 100 are easily envisioned, including medicinal delivery devices.

It is to be understood that the above description is intended to be illustrative, and not restrictive. For example, the above-described embodiments may be used in combination with each other. In addition, many modifications may be made to adapt a particular situation or material to the teachings of the invention without departing from its scope.

The invention claimed is:

1. An ultrasonic mist inhaler, comprising:
   a mouthpiece for inhaling a mist;
   a liquid reservoir structure comprising a liquid chamber adapted to receive liquid to be atomized;
   a sonication chamber in fluid communication with the liquid chamber, wherein at least part of the liquid reservoir structure and the mouthpiece form the sonication chamber, the sonication chamber comprising an ultrasonic vibration device; and
   a capillary element arranged between the liquid chamber and the sonication chamber, wherein the capillary element comprises a central portion and a peripheral portion, the central portion having a U-shape cross section extending to the sonication chamber, the U-shape cross section having an inner portion and an outer portion, the inner portion of the U-shape cross section being in a first plane and in surface contact with the ultrasonic vibration device and the outer portion of the U-shape cross section extending from the inner portion in a direction along a second plane transverse to the first plane and being not in surface contact with the ultrasonic vibration device.

2. The ultrasonic mist inhaler according to claim 1, wherein the ultrasonic mist inhaler comprises an inhalation channel, and wherein the inhalation channel comprises a frustoconical element arranged between the mouthpiece and the liquid reservoir structure.

3. The ultrasonic mist inhaler according to claim 2, wherein the inhalation channel comprises an inner container delimiting the sonication chamber and the liquid chamber.

4. The ultrasonic mist inhaler according to claim 3, wherein the inner container forms an inner wall of the liquid chamber.

5. The ultrasonic mist inhaler according to claim 4, wherein the mouthpiece comprise an inner duct receiving the frustoconical element.

6. The ultrasonic mist inhaler according to claim 1, further comprising an inner container delimiting the sonication chamber and the liquid chamber, wherein the inner container comprises a first section and a second section between which the capillary element is arranged.

7. The ultrasonic mist inhaler according to claim 6, wherein the capillary element has a flat shape extending from the sonication chamber to the liquid chamber.

8. The ultrasonic mist inhaler according to claim 1, wherein the peripheral portion has an L-shape cross section extending down to the liquid chamber.

9. The ultrasonic mist inhaler according to claim 1, wherein the ultrasonic vibration device is supported by an elastic member.

10. The ultrasonic mist inhaler according to claim 1, wherein the outer portion of the U-shape cross section has airflow apertures through which may pass a mist produced between the outer portion of the U-shape cross section and the ultrasonic vibration device.

11. The ultrasonic mist inhaler according to claim 1, wherein the liquid chamber contains a liquid comprising 57-70% (w/w) vegetable glycerin and 30-43% (w/w) propylene glycol, the propylene glycol including nicotine and flavorings.

* * * * *